United States Patent
Avitall

(10) Patent No.: US 9,314,631 B2
(45) Date of Patent: Apr. 19, 2016

(54) TONGUE SENSORS FOR MONITORING MULTIPLE PHYSIOLOGICAL PARAMETERS AND TONGUE STIMULATION

(71) Applicant: Boaz Avitall, Milwaukee, WI (US)

(72) Inventor: Boaz Avitall, Milwaukee, WI (US)

( * ) Notice: Subject to any disclaimer, the term of this patent is extended or adjusted under 35 U.S.C. 154(b) by 0 days.

(21) Appl. No.: 14/612,527

(22) Filed: Feb. 3, 2015

(65) Prior Publication Data
US 2015/0217115 A1 Aug. 6, 2015

Related U.S. Application Data

(60) Provisional application No. 61/935,154, filed on Feb. 3, 2014.

(51) Int. Cl.
| | | |
|---|---|---|
| *A61N 1/00* | (2006.01) | |
| *A61N 1/36* | (2006.01) | |
| *A61B 5/00* | (2006.01) | |
| *A61N 1/05* | (2006.01) | |
| *A61B 5/145* | (2006.01) | |
| *A61N 1/372* | (2006.01) | |
| *A61N 1/375* | (2006.01) | |

(52) U.S. Cl.
CPC ........ *A61N 1/36139* (2013.01); *A61B 5/14507* (2013.01); *A61B 5/682* (2013.01); *A61B 5/6867* (2013.01); *A61N 1/0548* (2013.01); *A61N 1/36085* (2013.01); *A61B 5/14532* (2013.01); *A61B 5/14542* (2013.01); *A61B 5/4818* (2013.01); *A61B 5/4836* (2013.01); *A61N 1/375* (2013.01); *A61N 1/37217* (2013.01)

(58) Field of Classification Search
CPC ............ A61N 1/36139; A61N 1/0548; A61N 1/36085; A61N 1/0558; A61N 1/059; A61B 5/14507; A61B 5/682; A61B 5/6867
See application file for complete search history.

(56) References Cited

U.S. PATENT DOCUMENTS

| | | |
|---|---|---|
| 6,598,006 B1 | 7/2003 | Honda et al. |
| 8,004,152 B2 | 8/2011 | Fung et al. |
| 8,044,766 B2 | 10/2011 | Ghovanloo et al. |
| 8,242,880 B2 | 8/2012 | Ghovanloo et al. |
| 2008/0190174 A1 | 8/2008 | Kooi et al. |

OTHER PUBLICATIONS

BIO-MEMS, Wikipedia, the free encyclopedia, http://en.wikipedia.org/wiki/Bio-MEMS, pp. 1-23.
Miller et al., Electrogustometric Thresholds: Relationship to Anterior Tongue Locus, Area of Stimulation, and Number of Fungiform Papillae, Physiological Behavior, Apr. 15, 2002, vol. 75(5), pp. 753-757.
Loucks and Doty, Effects of Stimulation Duration on Electrogustometric Thresholds, Physiology & Behavior, Mar. 2004, vol. 81, Issue 1, pp. 1-4.

*Primary Examiner* — Scott Getzow
(74) *Attorney, Agent, or Firm* — Nikolai & Mersereau, P.A.; C. G. Mersereau

(57) ABSTRACT

An implantable tongue sensor/stimulator device is disclosed for sensing and monitoring physiological parameters and providing a reactive stimulation to a patient. The device includes a main upper disc member carrying one or more micro-biomedical sensors for sensing multiple physiological parameters and one or more stimulation electrodes for creating stimulating sensations in the tongue, a lower tongue plate member that includes a battery for powering the device circuitry and a locking mechanism for locking the device in place when it is implanted, and an intermediate assembly including a central tongue rod member and conducting tubes for penetrating a tongue and connecting the upper disc with the lower disc. The device contains a wireless transmitter for transmitting data from the device.

16 Claims, 3 Drawing Sheets

Functional flow chart for multiple sensors and tongue stimulation

TONGUE SENSORS FOR MONITORING MULTIPLE PHYSIOLOGICAL PARAMETERS AND TONGUE STIMULATION

CROSS-REFERENCED TO RELATED APPLICATIONS

This application claims the benefit of U.S. Provisional Patent Application No. 61/935,154, filed Feb. 3, 2014, the disclosure of which is incorporated herein by reference in its entirety.

STATEMENT REGARDING FEDERALLY SPONSORED RESEARCH OR DEVELOPMENT

Not applicable

BACKGROUND OF THE INVENTION

I. Field of the Invention

The present invention relates generally to detecting and monitoring physiological parameters in patients. More particularly, the present invention is related to a system and technique for detecting and monitoring multiple physiological parameters that employs micro electro-mechanical systems or MEMS technology. Specifically, the system utilizes such technology in an attachable form to detect multiple physiological parameters from the surface of the tongue of a patient and communicates real time information regarding specific parameters to the associated patient and clinician. The system also can be used to stimulate the tongue to create real time biofeedback to the patient to assist in disease management and behavioral modification.

II. Related Art

Current wearable monitoring alerting devices do not provide real time information derived from contact with bodily fluids. Such communication has been limited to specialized implantable monitoring devices. Wearable devices heretofore have been quite limited in scope and dissemination of information.

It is known to use data input devices having multiple sensors to sense the physical position of a human tongue to control external equipment through the use of the tongue instead of a limb of the human body. Such devices are shown, for example, in U.S. Pat. Nos. 6,598,006, 8,044,766 and 8,242,880. An electronic tongue sensor for taste testing is disclosed in U.S. Pat. No. 8,004,152.

However, present devices have limited usefulness and it would present a distinct advantage if a wearable system were devised that could be based on the tongue of a patient and could be used to detect and monitor a plurality of physiological parameters from the surface of the tongue of a patient and communicate associated data on a real time basis to a patient and/or clinician.

SUMMARY OF THE INVENTION

By means of the present invention is an implantable tongue sensor/stimulator device for sensing and monitoring physiological parameters, recording and transmitting data and providing stimulation to the tongue of a patient in response to predetermined programmed sensed criteria. The device includes a main upper or main disc member and a lower or posterior tongue plate member joined by an intermediate assembly including an internal locking rod and tubing members which penetrate the tongue so that there is a disc member above and tongue plate member below the tongue when the implanted sensor/stimulator device is in place.

The main upper disc member includes upper or outer and lower or inner surfaces. The outer surface is provided with one or more, usually a plurality, of micro-biomedical sensors for sensing multiple physiological parameters in the mouth of a patient. The lower or inner surface of the disc member may be provided with sensors and includes one or more stimulation electrodes which contact the tongue and are used for creating stimulating sensations in the tongue which may affect feeling or taste. The lower tongue plate member includes a battery for powering the device circuitry and one or more reference electrodes. A locking mechanism is provided for locking the device in place when it is implanted. The intermediate assembly tongue locking rod member is utilized for penetrating the tongue for installing the implantable tongue sensor/stimulator device and connecting the main upper disc with the tongue plate member and locking mechanism. The intermediate assembly also contains a wireless transmitter for transmitting data from the device to a cell phone or other wireless receptor. The device may be made from a biocompatible polymer material which may be selected from polydimethylsiloxane (PDMS), poly (methyl methacrylate), or other suitable polymers or other materials, including biocompatible metals such as gold, silver, platinum and stainless steel.

The micro-biomedical sensors can be combined to make a plurality of diverse continuous or intermittent measurements of medical, biochemical, behavioral parameters of interest which may or may not have preprogrammed limits which, when exceeded, will trigger tongue stimulations affecting feeling or taste. The stimulation is designed to alert the individual to a triggered alarm in an effort to have the individual attempt to reverse the alarm. An example of such alarm may include in part; blood glucose levels, $CO_2$, $O_2$, salt intake, sugar intake, chewing rate, food consumption time interval, fluid intake, drug levels, levels of chemical species and others.

An associated tongue clip device may be used for determining a desired location on a tongue for implanting the device, for sensory receptors, mapping and testing.

DETAILED DESCRIPTION

Figure 1:
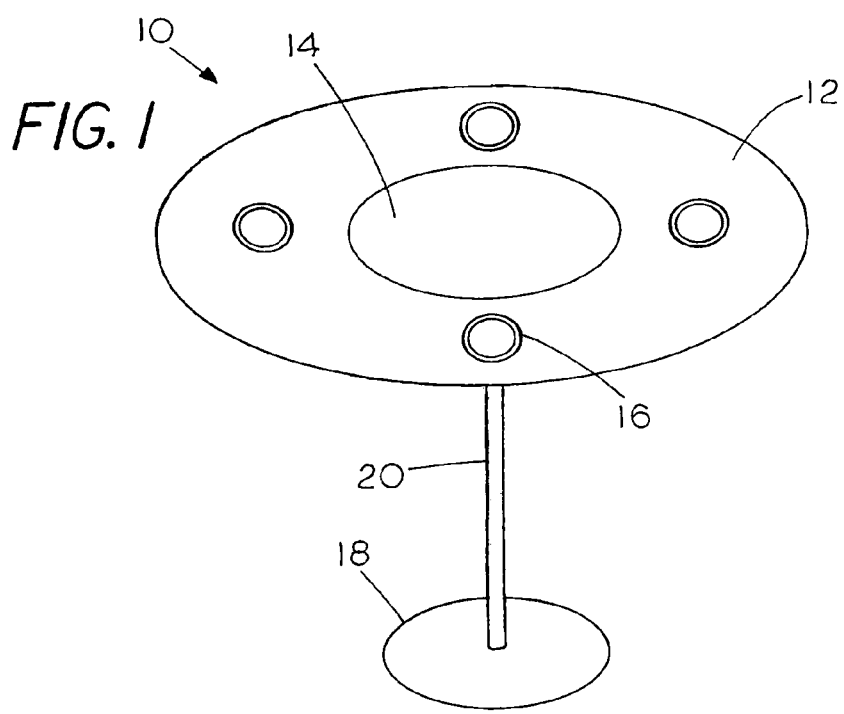
FIG. 1 is an enlarged schematic representation of an example of an embodiment of a tongue sensor/stimulator in accordance with the invention.

In the following detailed description, certain specific details are set forth to provide an understanding of the claimed subject matter. In conjunction with this, certain details that would be known to one having ordinary skill in the art may not be described in detail so as to focus on the inventive concepts. The description further is presented to illustrate the invention by way of example and not to limit the scope of the concepts in any manner.

The tongue sensors and stimulators of the present invention make use of integrated micro-circuit technology known as Micro-Electro-Mechanical Systems or MEMS, which are generally defined as miniaturized mechanical and electro-mechanical elements that are made using micro-fabrication techniques. Physical dimensions may be as small as one micron. The types of MEMS devices can also vary from relatively simple structures having no moving parts to extremely complex electro-mechanical systems controlled by micro-electronics. While these devices can take many forms, many are characterized as transducers and include microsensors and microactuators, which are devices that convert energy from one form to another.

Microsensors typically convert a measured mechanical or chemical signal to an electrical signal. A large number of such microsensors have been developed for almost every possible sensing modality, including temperature, pressure, chemical species, magnetic fields, radiation, pH, etc. Such devices have proved to be highly accurate, often outperforming corresponding macroscale counterparts.

Of particular interest in the present invention are plastic and polymer-based bio-MEMS, which have become very important in biological and physiological sensing. They have been developed for use in all types of biological applications. The most common polymers used in bio-MEMS include poly (methyl methacrylate) (PMMA), polydimethylsiloxane (PDMS), and SU-8 photoresist. They can be used in many kinds of mechanical detection and biochemical detection. Electrical and electro-chemical detectors have been adapted for portability and miniaturization. They include amperometric, potentiometric and conductiometric sensors. Amperometric biosensors measure redox electron currents from enzyme-catalyzed redox reactions. Potentiometric-type bio-sensors include ion-sensitive field effect transistors (ISFET), chemical field effect transistors (chem-FET), and light-addressable potentiometric sensors (LAPS). Conductometric devices measure changes in electrical impedance between two electrodes as a result of a biomolecular reaction. Optical detection may also be used in certain measurements.

It has been found that an array of micro-biomedical sensors may be combined on a device to make a plurality of diverse continuous or intermittent measurements of physiological parameters of interest. A plurality of types micro-biological sensors fabricated using MEMS technology can be combined and imbedded on a PDMS or other disc that is mounted on an attachable device such as a tongue-mounted sensor and stimulation device.

Figure 2:
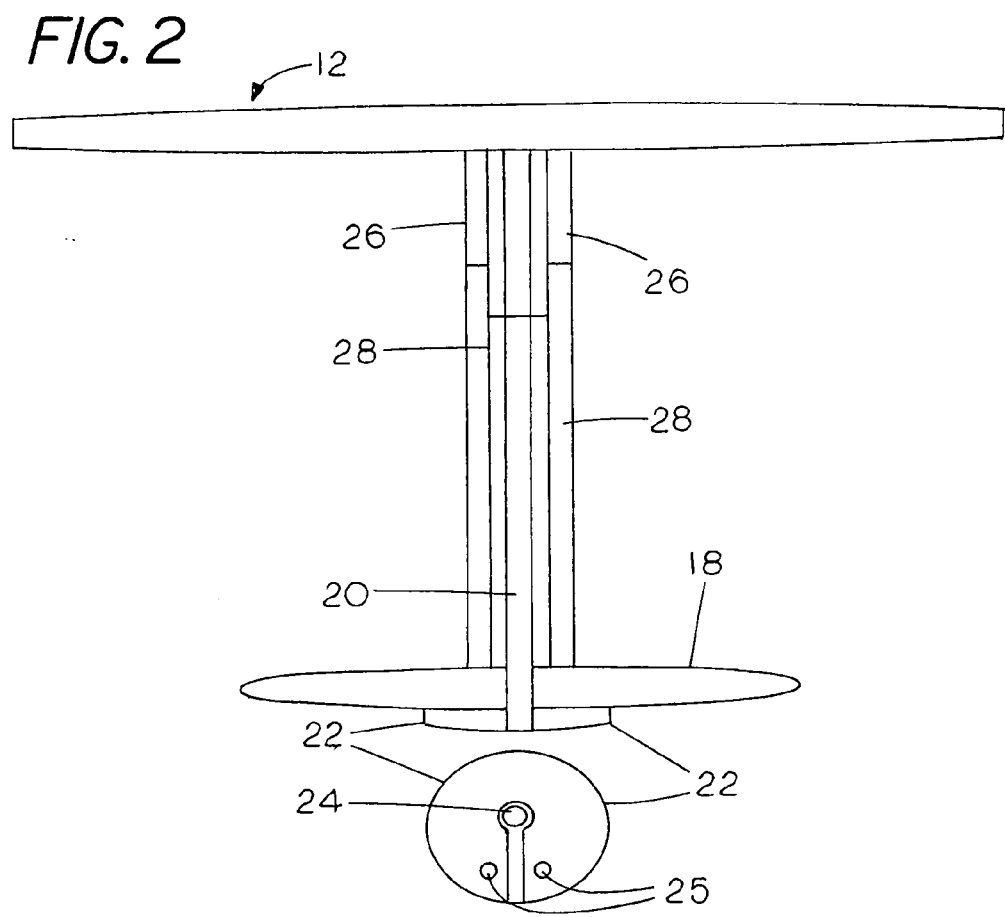
FIG. 2 is a further enlarged detailed schematic representation of a tongue sensor/stimulator in accordance with the invention.

A schematic example of a tongue sensor/stimulator device structure is shown generally at 10 in FIG. 1. It includes a main upper disc member or anterior tongue sensor stimulation plate 12 which may preferably be made of a plastic or polymer material that is biologically inert such as PDMS, PMMA, or the like, and contains an outer surface sensory transducer 14, which also may be made of PDMS, PMMA, or the like, and which carries an array of micro-biomedical sensors on the outer surface. The main upper disc member also includes a plurality of inner surface stimulation electrodes 16 and may include additional micro-biomedical sensors. The main upper disc member 12 is joined to a lower posterior tongue plate member 18 by an intermediate internal central locking rod member 20. As shown best in FIG. 2, the posterior tongue plate member 18 contains a battery (not shown) and is threaded onto rod member 20 and held in place by a locking plate member 22 which is secured to internal rod member 20 by a compression latch 24. Central locking rod member 20 is further provided with rings (not shown) to allow the use of compression latch 24 provided in locking plate 22. Holes 25 provided in locking plate 22 are used with a spreader tool to lock and remove the plate member 22.

The internal central locking rod member 20 surrounded by a plurality of associated tube members including tube members 26 and 28 which are electrical conductors connected to plates 12 and 18, respectively, by threaded connections. They are spaced from the central locking rod member 20 which can also serve as a reference electrode or conductor. The tube members 26 and 28 serve to deliver electric power from the battery in plate 18 to main upper disc or plate 12.

The central locking rod member with associate tube members is designed to penetrate and extend through a tongue on which the device is mounted and also contains a transmitter and functions as a transmitter and receiver antenna for wireless transmissions. The lower tongue plate member may also carry a variety of micro-biomedical sensors. In addition, tongue stimulations may be delivered across the thickness of the tongue.

Figure 3:
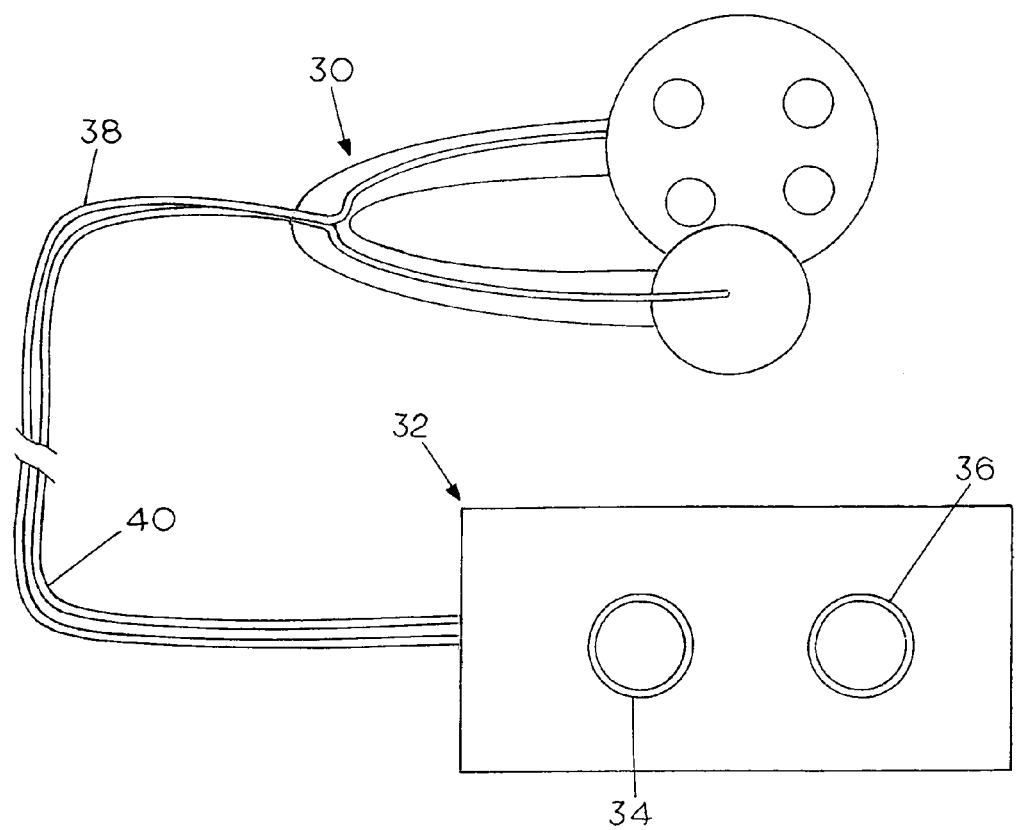
FIG. 3 is a schematic representation of a tongue clip for application to determine a selected localized stimulation site.

FIG. 3 depicts a schematic diagram of a tongue clip 30 for determining the best stimulation site for locating the tongue sensor/stimulator device on a tongue. A stimulation generator is shown at 32 which has frequency and amplitude controls 34 and 36. Lines 38 and 40 depict transmission of pulse signals and return signals, respectively.

Figure 4:
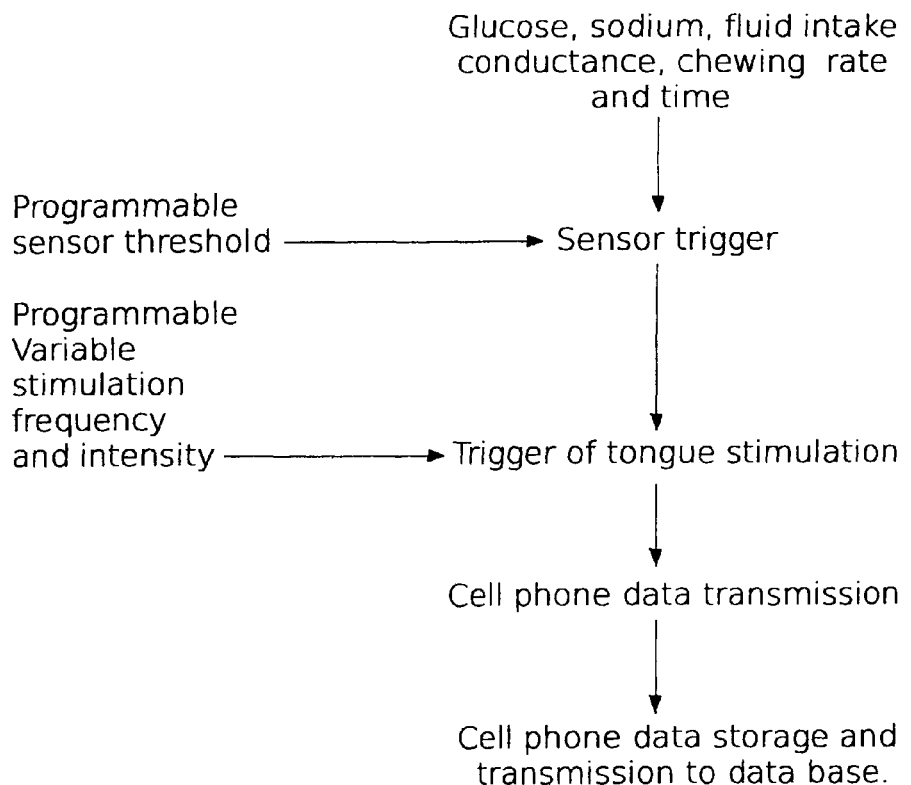
FIG. 4 is a functional flow chart for using multiple sensors to trigger tongue stimulation.

FIG. 4 shows a functional flow chart of a possible sensor/ stimulation combination using multiple sensors and a stimulation device along with wireless transmission and storage of data.

The functional flow chart shown in FIG. 4 is but one example of many possible combinations of a variety of sensors or tongue stimulation approaches. Thus, glucose, sodium, fluid intake changes in conductance, and chewing rate represent a set of variables to be sensed and monitored in a patient using the device of the invention. One or more of the variables may be given a preset programmed threshold to trigger sensor operation. A further threshold may be used to trigger one or more types of tongue stimulation. The circuitry is designed to be quite sophisticated and programmed to initiate multiple functions including wireless data transmission and reception and several types and levels of tongue stimulation.

The tongue stimulation aspect is a sophisticated system designed to interact with the patient. Tongue stimulation may be used for subtle messaging to the patient or aggressive tongue stimulation may be used to modify the patient's taste or even initiate pain, if needed, to enforce adherence with appropriate behavior to control a disease or to change a behavior.

Tongue stimulation may be designed to change the taste sensation in the mouth (with a specific setting of stimulation) or to create both unpleasant taste and pain to enhance behavioral modification to achieve: weight loss, diabetic monitoring to improve glucose control, fluid intake and mouth dryness for the purpose of monitoring heart failure, salt intake, Pulse Oximetery, and $CO_2/O_2$ sensing for sleep apnea, heart failure, asthma and COPD, sensing chewing rate, drug or chemical species levels and more. It is also postulated that varying the rate of pulsation, frequency and intensity of tongue stimulation will create a means of immediate communication with the patient. Stimulation intensity, frequency, duration, cycle length will be designed to create different tongue sensations to encourage compliance, reward or awareness for an action.

As indicated in FIG. 4, data transmission may be in the form of wireless communications as by cell phone communication for data storage and transmission.

This device is designed to be placed in the mouth to detect chemical concentration in the saliva, PH, electrolytes, gas concentrations, food intake composition, hydration and fluid intake. As indicated, the system utilizes MEMS technology to detect the above and other parameters and provide the patient and clinician (via cell phone communication) real time on-going status. Also, the system stimulates the tongue to create real time biofeedback to the patient and help enforce behavioral modification.

One example of the invention includes:
1. MEMS glucose sensor for diabetes management and weight loss
2. MEMS Conductance sensor for heart failure management functions including food and fluid intake
3. MEMS $CO_2$ and $O_2$, respiratory rate sensors, COPD, sleep apnea and heart failure management
4. MEMS pulse oximetry and heart rate sensor for heart failure management
5. MEMS temperature sensor to monitor infections
6. MEMS mechnosensor for assessing chewing rate and time for weight management
7. MEMS Potassium sensor Other sensors can be used for individual needs.

The continuous glucose monitor will sense the sugar levels in the mouth and once a pre-determined level is reached, it will trigger tongue stimulation. The intensity of the stimulation will be preset and programmable to change the taste in the mouth or trigger unpleasant sensation or pain in the mouth.

The device will collect and transmit glucose levels in the saliva over time and the relationship of tongue stimulation and glucose levels. This information will allow the dietitian, care giver, the patient (in some cases), other, to adjust the device function. Furthermore, this information may be used for behavioral modification research and understanding eating and other human behaviors.

Diabetes and/or weight management are examples of applications for the tongue sensing and stimulation device. After using the tongue clip 30 for localization of the best stimulation site, the tongue is pierced and the sensor/stimulator implanted. A high sugar-containing food is placed in the mouth and the sensor on the top of the tongue is triggered which, in turn, activates taste buds stimulation. Stimulation is optimized/adjusted post implantation to create a sour or bitter taste with the minimal amount of current. It may also trigger an unpleasant sensation or pain depending on the intensity and character of stimulation. The stimulation is adjusted to stop when the glucose concentration in the mouth/sensor plate is determined to be below a preset threshold level. This is likely to require the patient to rinse the mouth with water.

Stimulation intensity and frequency may be programmed to escalate depending on the response of the patient. Once it is implanted, the device cannot be removed by the patient and requires a specialized unlocking device to remove it.

Once removed, the device can be programmed to sense the change in impedance between electrodes and reduce power consumption or turn itself off to save battery power, but also to document removal (time/date stamp).

Of course, additional on-going measurements may be taken and the data recorded and/or transmitted by wireless communication. These may include, but are not limited to, chewing rate, saliva chemical analysis, fluid intake, mouth dryness, potassium, sodium, conductance and other parameters.

The specific or multi MEMS sensors using micro technology are embedded onto the outer or inner surface of the main upper disc member 12 and may also be located on the lower tongue plate member (depending on the specific function needed for the patient). The inner surfaces contact the tongue when the device is implanted. Conductance and stimulation electrodes are placed on the periphery of the disc. The disc is equipped with the rod 20, which serves as an antenna and is placed through the specific tongue area to be subjected to electrical stimulation. The lower or locking member 18 contains the battery and also serves as a reference electrode for stimulation.

Depending on the desired functionality, the technology can be constructed to address particular functional requirements. Cumulative data acquired over time may be used to track chronic conditions or habits of individuals. Certain measurements may be used to trigger responsive algorithms.

Furthermore, the tongue sensors may be programmed to collect data based on a predetermined programmed schedule (fixed intervals) or triggered by events (such as food intake, fluid intake, etc.). The data can be downloaded to a mobile recording unit (such as mobile phone) and, based on information, the mobile phone may communicate with the sensor and trigger tongue stimulation, as well as alarming caregivers, and/or the patient, etc. All such information can also be used to design therapeutic responses to many conditions.

The technology is not limited to the tongue and it will be recognized that such a system can be adapted to be used in other areas and may be inserted under the skin, for example, to sense multiple physiological parameters and transmit this information to a cell phone or other device. The device can also be programmed to stimulate the tissues for biofeedback and to cause a reaction from the patient.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:
1. An implantable tongue sensor/stimulator device for sensing and monitoring physiological parameters and providing stimulation to a patient comprising:
   (a) a main upper disc member carrying one or more micro-biomedical sensors for sensing multiple physiological parameters and one or more stimulation electrodes for creating stimulating sensations in the tongue and containing a wireless transmitter for transmitting data from the device;
   (b) a lower tongue plate assembly including a lower tongue plate, a power source for powering the device circuitry and a locking mechanism for locking the lower tongue plate in place on the device when it is implanted; and
   (c) an intermediate assembly including an internal central locking rod member, for extending through a tongue and connecting the main upper disc with the lower tongue plate both mechanically and electrically.

2. A device as in claim 1 wherein the main upper disc comprises a plurality of micro-biomedical sensors.

3. A device as in claim 1 wherein the main upper disc comprises a plurality of tongue stimulating electrodes.

4. A device as in claim 1 wherein the upper disc comprises a plurality of micro-biological sensors and a plurality of tongue stimulation electrodes.

5. A device as in claim 1 wherein the lower tongue plate member comprises one or more micro-biomedical sensors.

6. A device as in claim 1 further comprising an associated tongue clip for determining a desired location on a tongue for implanting the device.

7. A device as in claim 1 wherein the main upper disc comprises one or more sensors selected from the group consisting of temperature sensors, glucose sensors, conductance sensors, $CO_2$ and $O_2$, respiratory rate sensors, pulse oximetry and heart rate sensors, pH sensors, electrolyte sensors, gas concentration sensors, food intake composition sensors, hydration sensors, fluid intake sensors, mechanosensors for assessing chewing rate and time, sodium sensors and potassium sensors.

8. A device as in claim 1 wherein said main upper disc comprises one or more stimulation electrodes which are selected from the group consisting of electrodes which create a bitter or sour taste, an unpleasant sensation, or pain to the patient.

9. A device as in claim 1 wherein said one or more stimulator electrodes are activated based on one or more of said micro-biomedical sensors sensing a parameter which exceeds a predetermined programmed limit.

10. A device as in claim 1 wherein said main upper disc comprises one or more micro-biological sensors selected from the group of sensors which sense temperature, chewing rate, fluid intake, or mouth dryness.

11. A device as in claim 1 wherein the one or more stimulation electrodes is adjustable with regard to intensity and duration of stimulation.

12. A device as in claim 1 wherein the device comprises a polymeric material comprising PDMS, PMMA, or combinations thereof.

13. A device as in claim 1 wherein the device comprises a metallic material selected from gold, silver, platinum and stainless steel.

14. A device as in claim 1 wherein the device contains sensors on both the main upper disc and the lower tongue plate.

15. A method of sensing multiple physiological parameters and administering stimulation to a patient comprising:
(a) providing an implantable tongue sensor/stimulator device for sensing multiple physiological parameters and stimulating a patient comprising:
  (1) a main upper disc member carrying one or more micro-biomedical sensors for sensing multiple physiological parameters and one or more stimulation electrodes for creating stimulating sensations in the tongue;
  (2) a lower tongue plate member including a battery for powering the device circuitry and a locking mechanism for locking the device when it is implanted;
  (3) an intermediate tongue rod member for penetrating a tongue and connecting the main upper disc with the lower tongue plate and containing a wireless transmitter for transmitting data from the device;
(b) locating a desired tongue stimulation site on the tongue of a patient using a tongue clip;
(c) implanting said sensor/stimulator device at a site determined in (b);
(d) using said sensor/stimulator device to sense one or more physiological parameters; and
(e) applying stimulation to the tongue of the patient in response to sensor data being outside a programmed predetermined limit.

16. A method as in claim 15 comprising transmitting data from said one or more micro-biological sensors using wireless transmission.

* * * * *